US010832089B2

(12) United States Patent
Durrleman et al.

(10) Patent No.: US 10,832,089 B2
(45) Date of Patent: Nov. 10, 2020

(54) METHOD FOR DETERMINING THE TEMPORAL PROGRESSION OF A BIOLOGICAL PHENOMENON AND ASSOCIATED METHODS AND DEVICES

(71) Applicants:INSTITUT NATIONAL DE LA SANTE ET DE LA RECHERCHE MEDICALE (INSERM), Paris (FR); INSTITUT DU CERVEAU ET DE LA MOELLE EPINIERE, Paris (FR); ECOLE POLYTECHNIQUE, Palaiseau (FR); INRIA INSTITUT NATIONAL DE RECHERCHE EN INFORMATIQUE ET EN AUTOMATIQUE, Le Chesnay (FR); CENTRE NATIONAL DE LA RECHERCHE SCIENTIFIQUE, Paris (FR); SORBONNE UNIVERSITÉ, Paris (FR); ASSISTANCE PUBLIQUE-HOPITAUX DE PARIS, Paris (FR)

(72) Inventors: Stanley Durrleman, Paris (FR); Jean-Baptiste Schiratti, Palaiseau (FR); Stéphanie Allassonniere, Paris (FR); Olivier Colliot, Paris (FR)

(73) Assignees: INSTITUT NATIONAL DE LA SANTE ET DE LA RECHERCHE MEDICALE (INSERM), Paris (FR); INSTITUT DU CERVEAU ET DE LA MOELLE EPINIERE, Paris (FR); ECOLE POLYTECHNIQUE, Palaiseau (FR); INRIA INSTITUT NATIONAL DE RECHERCHE EN INFORMATIQUE ET AN AUTOMATIQUE, Le Chesnay (FR); CENTRE NATIONAL DE LA RECHERCHE SCIENTIFIQUE, Paris (FR); SORBONNE UNIVERSITÉ, Paris (FR); ASSISTANCE PUBLIQUE—HOPITAUX DE PARIS, Paris (FR)

( * ) Notice: Subject to any disclaimer, the term of this patent is extended or adjusted under 35 U.S.C. 154(b) by 107 days.

(21) Appl. No.: 16/300,391

(22) PCT Filed: May 11, 2016

(86) PCT No.: PCT/IB2016/052699
§ 371 (c)(1),
(2) Date: Nov. 9, 2018

(87) PCT Pub. No.: WO2017/194995
PCT Pub. Date: Nov. 16, 2017

(65) Prior Publication Data
US 2019/0138846 A1    May 9, 2019

(51) Int. Cl.
*G06K 9/00* (2006.01)
*G06K 9/62* (2006.01)
(Continued)

(52) U.S. Cl.
CPC ......... *G06K 9/6252* (2013.01); *G06K 9/6297* (2013.01); *A61B 5/4064* (2013.01);
(Continued)

(58) Field of Classification Search
CPC .................................................. G06K 2209/05
See application file for complete search history.

(56) References Cited

U.S. PATENT DOCUMENTS

2004/0242972 A1    12/2004    Adak et al.
2006/0235666 A1*   10/2006    Assa ...................... G01V 11/00
                                                         703/10
(Continued)

OTHER PUBLICATIONS

J.-B Schiratti et al: "Mixed-effects model for the spatiotemporal analysis of longitudinal manifold-valued data", Mathematical Foundations of Computational Anatomy, Oct. 9, 2015, pp. 48-59.
(Continued)

*Primary Examiner* — Oneal R Mistry
(74) *Attorney, Agent, or Firm* — Armstrong Teasdale LLP

(57) ABSTRACT

Provided herein is a method for determining the temporal progression of a biological phenomenon which may affect a studied subject, the method including the steps of providing
(Continued)

first data relative to biomarkers for the studied subject, the biomarkers being relative to the progression of the biological phenomenon, providing a numerical model, converting the first data into at least one point on the same Riemann manifold, and using a numerical model to determine a temporal progression for the biological phenomenon for the studied subject, the numerical model being a function in a Riemann manifold, the numerical model associating to values of biomarkers a temporal progression trajectory for the biological phenomenon and data relative to the dispersion of the progression trajectory for the biological phenomenon among a plurality of subjects, the numerical model being obtained by using a stochastic approximation in an expectation-maximization technique on data relative to biomarkers.

14 Claims, 10 Drawing Sheets

(51) Int. Cl.
  *G16H 50/30* (2018.01)
  *G16H 30/40* (2018.01)
  *A61B 5/00* (2006.01)
  *G06T 7/00* (2017.01)

(52) U.S. Cl.
  CPC ........ *G06K 2209/05* (2013.01); *G06T 7/0012* (2013.01); *G16H 30/40* (2018.01); *G16H 50/30* (2018.01)

(56) References Cited

U.S. PATENT DOCUMENTS

| | | | |
|---|---|---|---|
| 2009/0041314 A1* | 2/2009 | Vercauteren | G06K 9/00134 382/128 |
| 2012/0195984 A1* | 8/2012 | Lombard | A23L 33/175 424/722 |
| 2015/0198688 A1* | 7/2015 | Cetingul | G01R 33/56341 324/309 |

OTHER PUBLICATIONS

Bilgel Murat et al: "A multivariate nonlinear mixed effects model for longitudinal image analysis: Application to amyloid imaging", Neuroimage, Elsevier, Amsterdam, NL, vol. 134, Apr. 16, 2016, pp. 658-670.

International Search Report and Written Opinion for International Application No. PCT/IB2016/052699, dated Jan. 23, 2017, 10 pages.

* cited by examiner

Satiotemporal analysis of longitudinal manifold-valued data

METHOD FOR DETERMINING THE TEMPORAL PROGRESSION OF A BIOLOGICAL PHENOMENON AND ASSOCIATED METHODS AND DEVICES

CROSS-REFERENCE TO RELATED APPLICATIONS

This application is the national stage entry of PCT/IB2016/052699, filed on May 11, 2016, which is incorporated by reference in its entirety herein.

TECHNICAL FIELD OF THE INVENTION

The present invention concerns a method for determining the temporal progression of a biological phenomenon. The present invention also relates to an associated method for predicting, an associated method for diagnosing, an associated method for identifying a therapeutic target, an associated method for identifying a biomarker and an associated method for screening. The present invention also concerns a computer program product and a computer readable medium adapted to carry out one of these methods.

BACKGROUND OF THE INVENTION

Age-related brain diseases, such as Parkinson's or Alzheimer's disease are complex diseases, which have multiple effects on the metabolism, structure and function of the brain. Models of disease progression showing the sequence and timing of these effects during the course of the disease remain largely hypothetical. Large multimodal databases have been collected in the recent years in the hope to give experimental evidence of the patterns of disease progression based on the estimation of data-driven models. These databases are longitudinal, in the sense that they contain repeated measurements of several subjects at multiple time-points which do not necessarily correspond across subjects. As a matter of fact, learning models of disease progression from such databases raises great methodological challenges.

The main difficulty lies in the fact that the age of a given individual gives no information about the stage of disease progression of this individual. The first clinical symptoms of Alzheimer's disease may appear at forty years for one patient and eighty years for another. The duration of the disease also may vary across patients from few years to decades. Moreover, the onset of the disease does not correspond with the onset of the symptoms: according to recent studies, symptoms are likely to be preceded by a silent phase of the disease, for which little is known. As a consequence, statistical models based on the regression of measurements with age are inadequate to model disease progression.

SUMMARY OF THE INVENTION

The invention aims at determining the temporal progression of a biological phenomenon, notably a neurodegenerative disease, based on data taken from a subject.

To this end, the invention concerns a method for determining the temporal progression of a biological phenomenon which may affect a studied subject, the method comprising the step of providing first data, the first data being data relative to biomarkers for the studied subject, the biomarkers being relative to the progression of the biological phenomenon, the step of providing a numerical model, the numerical model being a function in a Riemann manifold, the numerical model associating to values of biomarkers a temporal progression trajectory for the biological phenomenon and data relative to the dispersion of the progression trajectory for the biological phenomenon among a plurality of subjects, the numerical model being obtained by using a stochastic approximation in an expectation-maximization technique on data relative to biomarkers taken at different time points for a plurality of subjects, the step of converting the first data into at least one point on the same Riemann manifold, and the step of using the numerical model to determine a temporal progression for the biological phenomenon for the studied subject.

The present invention enables to determine the temporal progression of a biological phenomenon based on data taken from a subject.

The data taken from the subject are data relative to biomarkers for the studied subject, the biomarkers being relative to the progression of the biological phenomenon.

There is little constraint on the data taken from the subject which enables to carry out the method with data taken from the subject different from the data used to build the numerical model. The only constraint is that the data taken from the subject and the data used to build the numerical model be relative to the same biomarker(s).

The converting step ensures such freedom.

In addition, the numerical model enables to obtain interesting result by proposing a generic statistical framework for the definition and estimation of mixed-effects models for longitudinal manifold-valued data. Using the tools of geometry allows us to derive a method that makes little assumptions about the data and problem to deal with. Modeling choices boil down to the definition of the metric on the manifold. This geometrical modeling also allows us to introduce the concept of parallel curves on a manifold, which is a key to decompose differences seen in the data in a unique manner into a spatial and a temporal component. Because of the non-linearity of the model, the estimation of the parameters shall be based on an adequate maximization of the observed likelihood. To address this issue, a stochastic version of the Expectation-Maximization algorithm is used.

According to further aspects of the invention which are advantageous but not compulsory, the method for determining the temporal progression of a biological phenomenon might incorporate one or several of the following features, taken in any technically admissible combination:

- the biological phenomenon is a biological phenomenon whose temporal progression extends over more than three years.
- the biological phenomenon is a neurodegenerative disease.
- at the step of providing first data, the first data are data relative to neuropsychological biomarkers.
- the studied subject is an animal, preferably a mammal, more preferably a human being.
- at the step of providing the numerical model, the stochastic approximation in an expectation-maximization technique is a Monte-Carlo Markov Chain Stochastic Approximation Expectation-Maximization technique.
- at the step of providing the numerical model, the number of subjects is superior or equal to 100.
- in the numerical model, the data relative to the dispersion of the progression trajectory for the biological phenomenon among a plurality of subjects are provided as standard deviations of time for a plurality of values of biomarkers.

The invention also concerns to a method for predicting that a subject is at risk of suffering from a disease, the method for predicting at least comprising the step of carrying out the steps of the method for determining the temporal progression of a biological phenomenon which may affect a studied subject as previously described, the biological phenomenon being the disease, to obtain a first temporal progression, and the step of predicting that the subject is at risk of suffering from the disease based on the first temporal progression.

The invention also relates to a method for diagnosing a disease, the method for diagnosing at least comprising the step of carrying out the steps of the method for determining the temporal progression of a biological phenomenon which may affect a studied subject as previously described, the biological phenomenon being the disease, to obtain a first temporal progression, and the step of diagnosing the disease based on the first temporal progression.

The invention also concerns to a method for identifying a therapeutic target for preventing and/or treating a pathology, the method comprising the steps of carrying out the method for determining the temporal progression of a biological phenomenon which may affect a studied subject as previously described, the first data being data relative to a subject suffering from the pathology, to obtain a first temporal progression, carrying out the method for determining the temporal progression of a biological phenomenon which may affect a studied subject as previously described, the first data being data relative to a subject not suffering from the pathology, to obtain a second temporal progression, selecting a therapeutic target based on the comparison of the first and second temporal progressions.

The invention also relates to a method for identifying a biomarker the biomarker being a diagnostic biomarker of a pathology, a susceptibility biomarker of a pathology, a prognostic biomarker of a pathology or a predictive biomarker in response to the treatment of a pathology, the method comprising the steps of carrying out the method for determining the temporal progression of a biological phenomenon which may affect a studied subject as previously described, the first data being data relative to a subject suffering from the pathology, to obtain a first temporal progression, carrying out the method for determining the temporal progression of a biological phenomenon which may affect a studied subject as previously described, the first data being data relative to a subject not suffering from the pathology, to obtain a second temporal progression, selecting a biomarker based on the comparison of the first and second temporal progressions.

The invention also relates to a method for screening a compound useful as a medicine, the compound having an effect on a known therapeutical target, for preventing and/or treating a pathology, the method comprising the steps of carrying out the method for determining the temporal progression of a biological phenomenon which may affect a studied subject as previously described, the first data being data relative to a subject suffering from the pathology and having received the compound, to obtain a first temporal progression, carrying out the method for determining the temporal progression of a biological phenomenon which may affect a studied subject as previously described, the first data being data relative to a subject suffering from the pathology and not having received the compound, to obtain a second temporal progression, selecting a compound based on the comparison of the first and second temporal progressions.

The invention also relates to a computer program product comprising instructions for carrying out the steps of a method as previously described, when said computer program product is executed on a suitable computer device. The invention also relates to a computer readable medium having encoded thereon a computer program product as previously described.

BRIEF DESCRIPTION OF THE DRAWINGS

The invention will be better understood on the basis of the following description which is given in correspondence with the annexed figures and as an illustrative example, without restricting the object of the invention. In the annexed figures.

DETAILED DESCRIPTION OF SOME EMBODIMENTS

Figure 1:
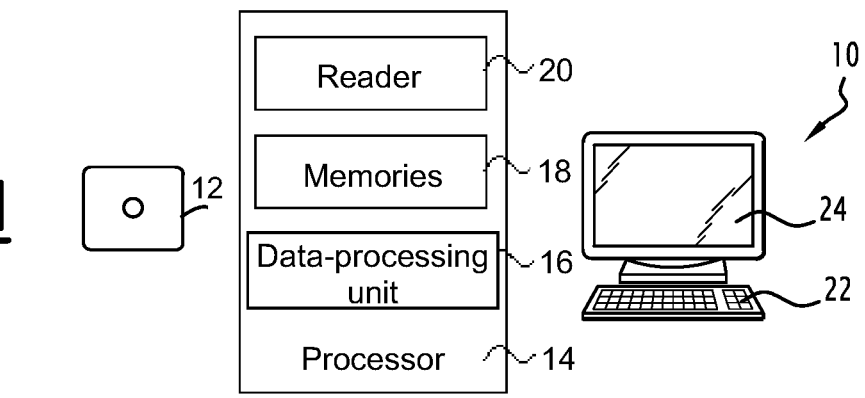
FIG. 1 shows schematically a system and a computer program product whose interaction enables to carry out a method for determining the temporal progression of a biological phenomenon.
Figure 2:
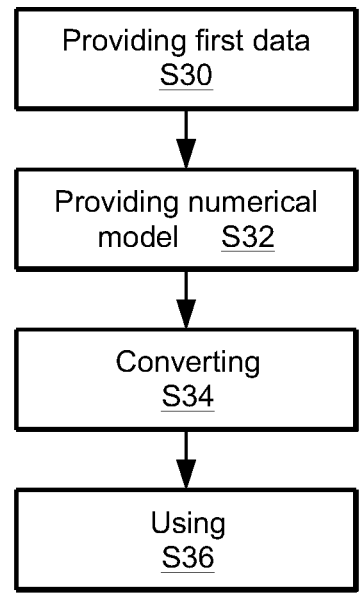
FIG. 2 shows a flowchart of an example of carrying out a method for determining the temporal progression of a biological phenomenon.

A system 10 and a computer program product 12 are represented in FIG. 1. The interaction between the computer program product 12 and the system 10 enables to carry out a method for determining the temporal progression of a biological phenomenon.

System 10 is a computer. In the present case, system 10 is a laptop.

More generally, system 10 is a computer or computing system, or similar electronic computing device adapted to manipulate and/or transform data represented as physical, such as electronic, quantities within the computing system's registers and/or memories into other data similarly represented as physical quantities within the computing system's memories, registers or other such information storage, transmission or display devices.

System 10 comprises a processor 14, a keyboard 22 and a display unit 24.

The processor 14 comprises a data-processing unit 16, memories 18 and a reader 20. The reader 20 is adapted to read a computer readable medium.

The computer program product 12 comprises a computer readable medium.

The computer readable medium is a medium that can be read by the reader of the processor. The computer readable medium is a medium suitable for storing electronic instructions, and capable of being coupled to a computer system bus.

Such computer readable storage medium is, for instance, a disk, a floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

A computer program is stored in the computer readable storage medium. The computer program comprises one or more stored sequence of program instructions.

The computer program is loadable into the data-processing unit 16 and adapted to cause execution of the method for determining the temporal progression of a biological phenomenon when the computer program is run by the data-processing unit 16.

Operation of the system 10 is now described in reference to an example of carrying out of a method for determining the temporal progression of a biological phenomenon which may affect a studied subject.

The studied subject is an animal.

Preferably, the studied subject is a mammal.

More preferably, the studied subject is a human being.

For the sake of exemplification, it is assumed, in the remainder of the specification, that the studied subject is a human being.

In the most generic definition, the biological phenomenon is a biological phenomenon for which a temporal progression can be defined.

For instance, a disease or the ageing are examples for which a temporal progression can be defined.

According to a specific embodiment, the biological phenomenon is a biological phenomenon whose temporal progression extends over more than three years.

According to a more specific embodiment, the biological phenomenon is a biological phenomenon whose temporal progression extends over more than ten years.

In addition, at least one of the onset of the biological phenomenon or the duration of the biological phenomenon varies from a subject to another.

A typical example for such biological phenomenon is a neurodegenerative disease.

Neurodegenerative disease designates a set of disease which primarily affects the neurons in the human brain.

Alzheimer's disease, Parkinson's disease, prion disease, motor neurone disease, Huntington's disease, spinocerebellar ataxia and spinal muscular atrophy are examples of neurodegenerative diseases.

For the sake of exemplification, it is assumed, in the remainder of the specification, that the biological phenomenon is Alzheimer's disease.

The method for determining comprises four steps: a step S30 of providing first data, a step S32 of providing a numerical model, a step S34 of converting and a step S36 of using.

At step S30, first data are provided.

The first data are data relative to biomarkers for the studied subject.

The biomarkers are relative to the progression of the biological phenomenon.

For instance, the first data are data collected via cognitive tests devoted to detect the Alzheimer's disease.

According to another embodiment, the first data are data obtained by medical imaging.

According to still another embodiment, the first data are a combination of data collected by different ways. As an example, the first data are data collected via cognitive tests and data by medical imaging.

Preferably, the first data are data collected at several time points for the same subject.

In the specific described example, the first data are data relative to neuropsychological biomarkers, for instance assessing cognitive or motor functions such as memory or praxis.

At step S32, a numerical model labeled NM is provided.

The numerical model NM is a function in a Riemann manifold named RM.

The numerical model NM associates to values of biomarkers a temporal progression trajectory for the biological phenomenon and data relative to the dispersion of the progression trajectory for the biological phenomenon among a plurality of subjects.

According to a preferred embodiment, the data relative to the dispersion of the progression trajectory for the biological phenomenon among a plurality of subjects are provided as standard deviations of time for a plurality of values of biomarkers.

The numerical model NM is therefore construable as a statistical model.

The numerical model NM is obtained by using a stochastic approximation in an expectation-maximization technique on data relative to biomarkers taken at different time points for a plurality of subjects.

This means that the numerical model NM concerns longitudinal data.

Figure 3:
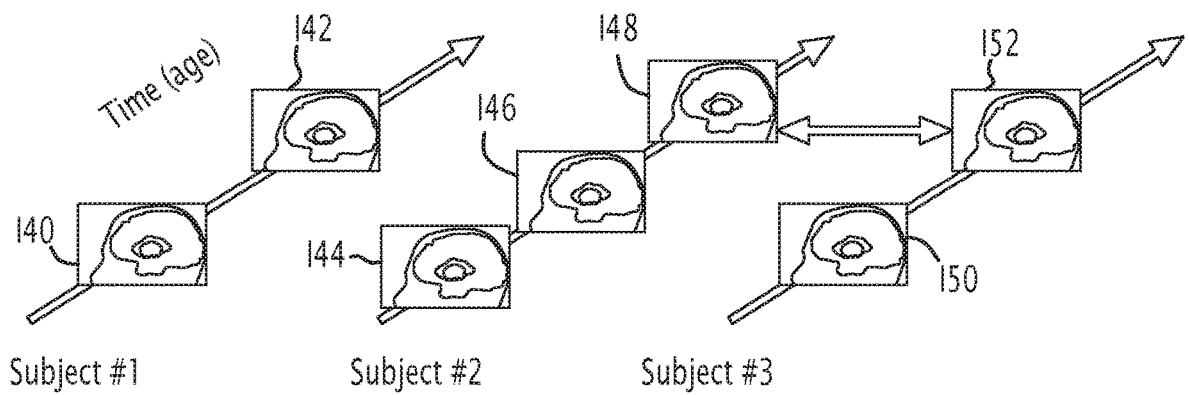
FIG. 3 shows schematically an example of longitudinal manifold-valued data.

FIG. 3 illustrates a specific example of longitudinal data.

For each subject, several images of their brain are taken at different instants.

More precisely, for subject 1, two images I40 and I42 are provided.

For subject 2, three images I44, I46 and I48 are provided.

For subject 3, two images I50 and I52 are provided.

Except for images I48 and I52 (as schematically illustrated by the arrow on FIG. 3), the images are taken at different time points.

The case of FIG. 3 is purely illustrative, the longitudinal data being usually more numerous.

Indeed, preferably, the number of subjects is superior or equal to 100.

In other words, the data consists in repeated multivariate measurements of p individuals. For a given individual, the measurements are obtained at time points $t_{i,1} < \ldots < t_{i,ni}$. The j-th measurement of the i-th individual is denoted by $y_{i,j}$. In the remainder of the specification, it is assumed that each observation $y_{i,j}$ is a point on a N-dimensional Riemannian manifold $\mathbb{M}$ embedded in $\mathbb{R}^N$ and equipped with a Riemannian metric $g^{\mathbb{M}}$.

The generic spatiotemporal model belongs to a class of statistical models for which maximum likelihood estimates cannot be obtained in closed form. This issue is addressed by using a stochastic approximation in a expectation-maximization technique.

Preferably, the stochastic approximation in an expectation-maximization technique is a Monte-Carlo Markov Chain Stochastic Approximation Expectation-Maximization technique.

Figure 4:
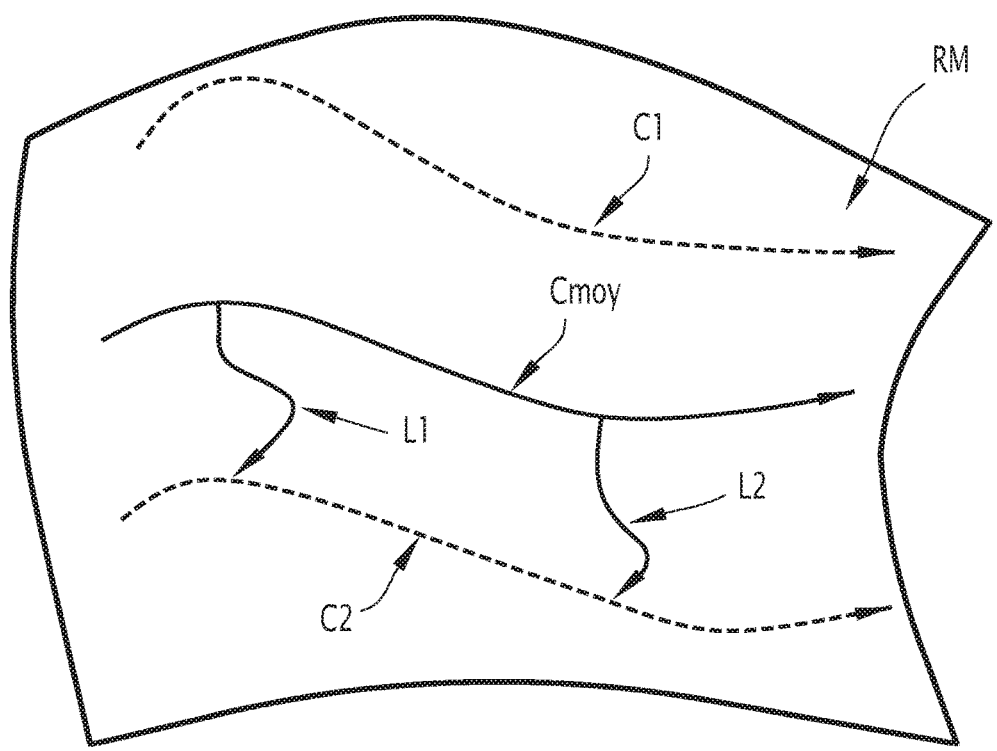
FIG. 4 shows schematically an example of numerical model in a Riemann manifold.

An example of the numerical model NM provided at the step S32 is schematically represented on FIG. 4.

The numerical model NM can be provided by providing three curves which are $C_{moy}$, $C_1$ and $C_2$. The three curves correspond to three kinds of temporal progression for the Alzheimer's disease. These curves may represent the average disease progression trajectory ($C_{moy}$) and the dispersion of this trajectory at plus or minus one standard deviation in the values of biomarkers for a plurality of subjects ($C_1$ and $C_2$).

Two curves L1 and L2 are represented on FIG. 4. These curves indicate a temporal correspondence between the mean curve $C_{moy}$ and the second curve $C_2$.

Figure 5:
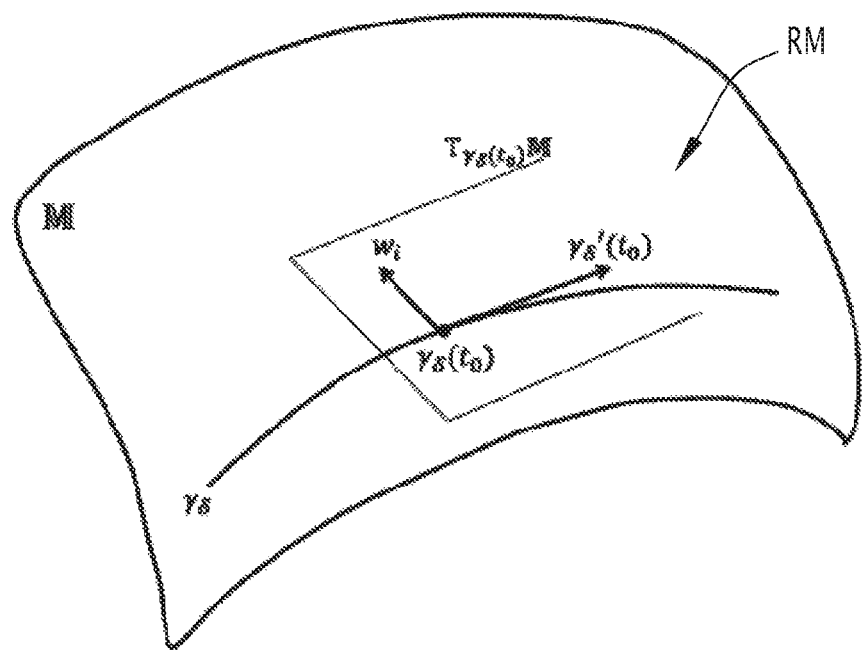
FIGS. 5 to 7 shows schematically calculation in the Riemann manifold so as to obtain another example of numerical model.
Figure 6:
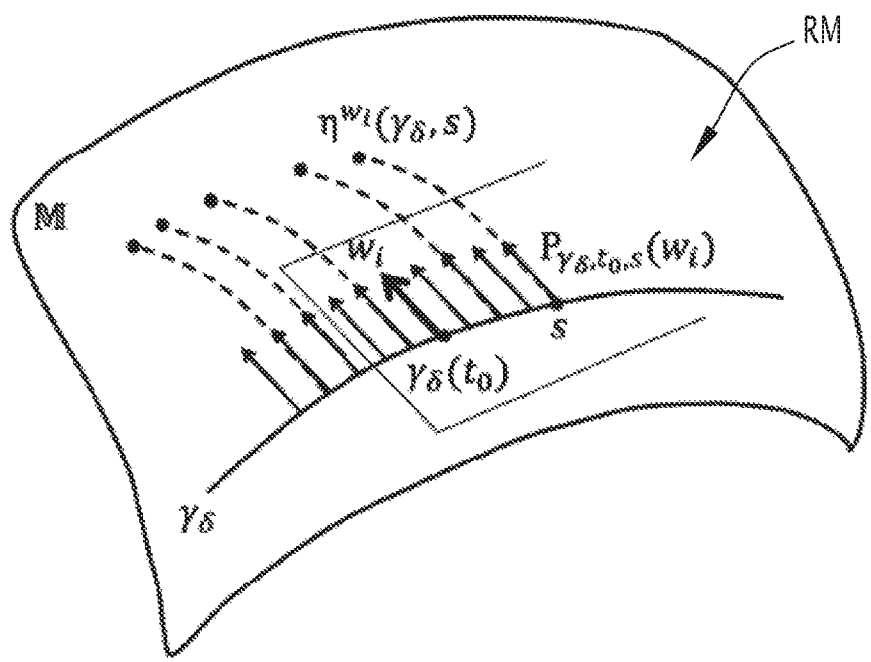
Figure 7:
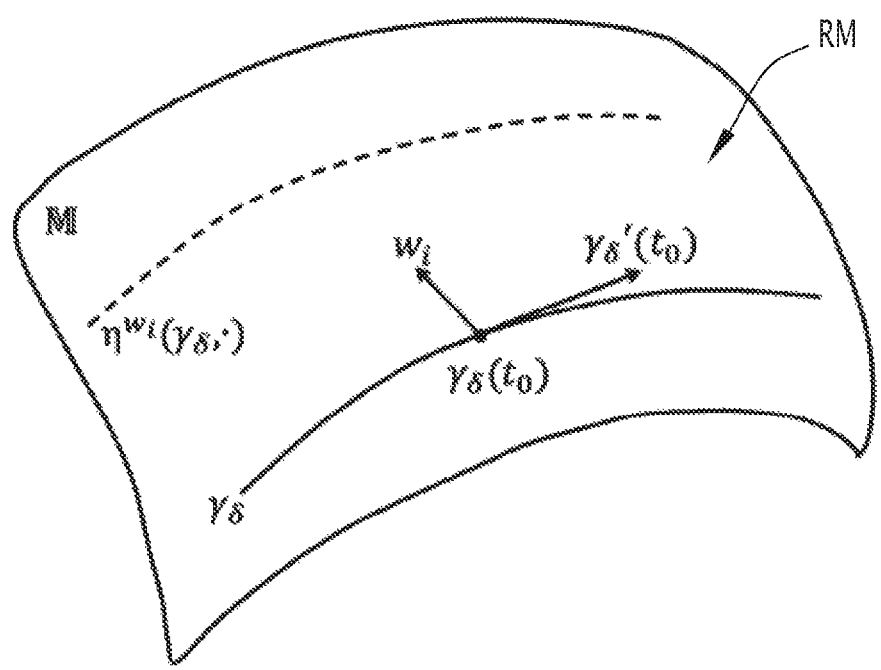

As a specific example, in relation to FIGS. 5 to 7, it is now illustrated how to obtain a specific numerical model NM relevant for the Alzheimer's disease.

Let ($\mathbb{M}, g^{\mathbb{M}}$) be a Riemannian manifold of dimension N equipped with a Riemannian metric $g^{\mathbb{M}}$, which is assumed to be geodesically complete.

A Riemannian metric is geodesically complete if the geodesics of $\mathbb{M}$ are defined on $\mathbb{R}$, this notation being for the set of real numbers. It is recalled that a geodesic is a curve drawn on the manifold $\gamma: \mathbb{R} \to \mathbb{M}$, which has no acceleration.

The Riemannian metric $g^{\mathbb{M}}$ defines a unique affine connexion on $\mathbb{M}$, namely the Levi-Civita connexion, denoted by $\nabla^{\mathbb{M}}$. Let $\gamma$ denote a geodesic of $\mathbb{M}$ and $t_0 \in \mathbb{R}$. It is recalled that, given a tangent vector $\xi$ in $T_{\gamma(t_0)}\mathbb{M}$, the parallel transport of $\xi$ along $\gamma$, denoted by $X(s) = P_{\gamma,t_0,s}(\xi)$ is a vector field along $\gamma$ which satisfies the following equations:

$$X(t_0) = \xi \text{ and } \nabla^{\mathbb{M}} X(s) = 0$$

Let $p \in \mathbb{M}$.

The Riemannian exponential in $\mathbb{M}$ at p is denoted by $exp_p^{\mathbb{M}}$.

For $v \in T_p \mathbb{M}$, $exp_p^{\mathbb{M}}(v)$ denotes the value at time 1 of the geodesic in $\mathbb{M}$ issued from p with initial velocity v.

The temporal progression of a family of N (N≥2) scalar biomarkers is studied. A longitudinal dataset of the form $(y_{i,j}, t_{i,j})_{ij}$ is considered. This longitudinal dataset is obtained by observing p individuals at repeated time points. The vector $y_{i,j}$ denotes the j-th observation ($1 \leq j \leq n_i$) of the i-th individual. The k-th coordinate of $y_{i,j}$, denoted by $y_{i,j,k}$, corresponds to the measurement of the k-th biomarker, at time $t_{i,j}$.

It is assumed that each measurement $y_{i,j,k}$ belongs to a one dimensional Riemannian manifold (M, g) which is geodesically complete. In this setting, the observations $y_{i,j} = (y_{i,j,1}, \ldots, y_{i,j,N})$ can be considered as points in the product manifold $\mathbb{M} = M^N$. The average progression of this family of biomarkers is modeled by a geodesic trajectory on the manifold M, which is equipped with the product metric, denoted by $g^{\mathbb{M}}$.

The numerical model NM is described for observations on a manifold which is a product of one-dimensional manifolds. This framework is particularly convenient to analyze the temporal progression of a family of biomarkers.

In order to determine relative progression of the biomarkers among themselves, the average trajectory is chosen among the parametric family of geodesics:

$$(t \to (\gamma_0(t), \gamma_0(t+\delta_1), \ldots, \gamma_0(t+\delta_{N-1})))_\delta$$

where:

$\delta = (0, \delta_1, \ldots, \delta_{N-1})$ and $\gamma_0$ is a geodesic, of the one-dimensional manifold M, parametrized by a point $p_0$ in M, a time $t_0$ and a velocity $v_0$ in $T_{p_0}M$.

This parametrization of the geodesic $\gamma_0$ is the natural parametrization such that:

$$\gamma_0(t_0) = p_0 \text{ and } \dot{\gamma}_0(t_0) = v_0$$

By choosing the average trajectory among this parametrized family of geodesics, it is assumed that, on average, the biomarkers follow the same trajectory but shifted in time. The delay between the progression of the different biomarkers is measured by the vector $\delta = (0, \delta_1, \ldots, \delta_{N-1}) \in \mathbb{R}^N$. The parameters $\delta_i$ ($1 \leq i \leq N-1$) measure a relative delay between two consecutive biomarkers. The parameter $t_0$ plays the role of reference time as the trajectory of the first biomarker will reach the value $p_0$ at time $t_0$ whereas the other trajectories will reach the same value $p_0$ at different points in time, shifted with respect to the time $t_0$.

The numerical model NM is a hierarchical model: data points are assumed to be sampled from subject-specific trajectories of progression. These individual trajectories are derived from the average trajectory $\gamma_\delta$. The subject-specific trajectory of the i-th individual is constructed by considering a non-zero tangent vector $w_i$ in $T_{\gamma_\delta(t_0)}\mathbb{M}$, orthogonal to $\dot{\gamma}_\delta(t_0)$ for the inner product defined by the metric ($\langle ., . \rangle_{\gamma_\delta(t_0)} = g_{\gamma_\delta(t_0)}^{\mathbb{M}}$). This tangent vector $w_i = (w_{1,i}, \ldots, w_{N,i})$ is a space shift which enables registering the individual trajectories in the space of measurements. The tangent vector $w_i$ is transported along the geodesic $\gamma_\delta$ from time $t_0$ to time s using parallel transport. This transported tangent vector is denoted by $P_{\gamma,t_0,s}(w_i)$. At the point $\gamma_\delta(s)$, a new point in $\mathbb{M}$ is obtained by taking the Riemannian exponential of $P_{\gamma,t_0,s}(w_i)$. This new point is denoted by $\eta^{w_i}(\gamma_\delta, s)$. As s varies, this point describes the curve $s \to \eta^{w_i}(\gamma_\delta, s)$, which is considered as a "parallel" to the curve $y_\delta$ (see FIG. 5). The orthogonality condition on the tangent vectors $w_i$ is an important hypothesis which ensures that a point $\eta^{w_i}(\gamma_\delta, s)$ on a parallel moves at the same pace on this parallel than on the average trajectory. This hypothesis ensures the uniqueness of the decomposition between spatial and temporal components.

The trajectory $\gamma_i$ of the i-th individual is obtained by reparametrizing the parallel $\eta^{w_i}(\gamma_\delta, \cdot): \gamma_i(s) = \eta^{w_i}(\gamma_\delta, \psi_i(s))$, where the mapping $\psi_i(s) = \alpha_i(s - t_0 - \tau_i) + t_0$ is a subject-specific affine reparametrization which allows registering in time the different individual trajectories of progression. Such affine reparametrization corresponds to a time-warp wherein the tangent vector $w_i$ can be considered, in the light of the univariate model, as a random effect associated to the point $p_0$.

The parameter $\alpha_i$ is an acceleration factor which encodes whether the i-th individual is progressing faster or slower than the average, $\tau_i$ is a time-shift which characterizes the advance or delay of the ith individual with respect to the average and $w_i$ is a space-shift which encodes the variability in the measurements across individuals at a given stage, once the paces at which individual trajectories are followed are normalized. Each of these parameters are assumed to be random, non observed and variables.

Because $\mathbb{M}$ is equipped with the product metric, the parallel transport of the tangent vector $w_i \in T_{\gamma_\delta(t_0)}\mathbb{M}$ is a N-dimensional vector whose k-th ($1 \leq k \leq N$) component is equal to the parallel transport of the tangent vector $w_{k,j} \in T_{\gamma_0(\cdot + \delta_{k-1})}M$ along the curve $s \to \gamma_0(s + \delta_{k-1})$ in the one-dimensional manifold M. It follows that:

$$P_{\gamma,t_0,s}(w_i) = \left( \frac{w_{1,i}}{\dot{\gamma}_0(t_0)} \dot{\gamma}_0(s), \ldots, \frac{w_{N,i}}{\dot{\gamma}_0(t + \delta_{N-1})} \dot{\gamma}_0(s + \delta_{N-1}) \right)$$

Taking the Riemanniann exponential, in $\mathbb{M}$, of the tangent vector $P_{\gamma,t_0,s}(w_i)$ boils down to taking the Riemannian exponential, in M, of each component of the vector. If $exp^{\mathbb{M}}$ denotes the Riemannian exponential map in M, the k-th ($1 \leq k \leq N$) component of $\eta^{w_i*}\gamma_\delta, s)$ is given by:

$$exp_{\gamma_0(s+\delta_{k-1})}^{\mathbb{M}} \left[ \frac{w_{k,i}}{\dot{\gamma}_0(t_0 + \delta_{k-1})} \dot{\gamma}_0(s + \delta_{N-1}) \right] = \gamma_0\left( s + \delta_{k-1} + \frac{w_{k,i}}{\dot{\gamma}_0(t_0 + \delta_{k-1})} \right)$$

For the longitudinal dataset $(y_{i,j}, t_{i,j})$ $(1 \leq i \leq p, 1 \leq j \leq n_i)$, the numerical model NM writes:

$$y_{i,j} = y_i(t_{i,j}) + \varepsilon_{i,j}$$

In particular, for the k-th biomarker, this numerical model NM writes:

$$y_{i,j,k} = \gamma_0 \left( \frac{w_{k,i}}{\dot{\gamma}_0(t_0 + \delta_{k-1})} + t_0 + \alpha_i(s - t_0 - \tau_i) + \delta_{k-1} \right) + \varepsilon_{i,j,k}$$

Wherein:
$\alpha_i = \exp(\eta_i)$ with $\eta_i$ is assumed to follow a probability distribution $\mathcal{N}(0, \sigma_\eta^2)$, $\mathcal{N}$ being the Gaussian distribution with zero mean and variance $\sigma_\eta^2$, $\tau_i$ is assumed to follow a probability distribution according to $\mathcal{N}(0, \sigma_\tau^2)$, $\sigma_\tau^2$ being the variance of the Gaussian distribution, $\varepsilon_{i,j}$ is assumed to follow a probability distribution according to $\mathcal{N}(0, \sigma^2 . I_n)$, $\sigma^2$ being the variance of the Gaussian distribution and $I_n$ the identity matrix of order n, and the tangent vectors $w_i$ are assumed to be a linear combination of $N_s < N$ statistically independent components. This writes $w_i = A.s_i$ where A is a $N \times N_s$ matrix of rank $N_s$ whose columns are vectors in $T_{\gamma_\delta(t_0)} \mathbb{M}$ and $s_i$ is a vector of $N_s$ independent sources following a Laplace distribution with parameter 1/2.

As a consequence, the fixed effects of the model are the parameters of the average geodesic: the point $p_0$ on the manifold, the time-point $t_0$ and the velocity $v_0$. The random effects are the acceleration factors $\alpha_i$, time-shifts $\tau_i$ and space-shifts $w_i$. The random effects $z = (\eta_i, \tau_i, s_{j,i})$ $(1 \leq i \leq p$ and $1 \leq j \leq N_s)$ are considered as hidden variables. With the observed data $y = (y_{i,j,k})_{i,j,k}$, $(y, z)$ form the complete data of the model. In this context, the Expectation-Maximization (EM) algorithm is very efficient to compute the maximum likelihood estimate of the parameters of the model, denoted $\theta$.

In other words, it appears that the numerical model NM depends from the vector parameter $\theta$ which writes:

$$\theta = (p_0, t_0, v_0, \delta, \sigma_\eta, \sigma_\tau, \sigma, vec(A))$$

where vec(A) stands for the entries of the matrix A concatenated in a raw vector.

In addition, the random effects of the model are described by $(\alpha_i, \tau_i, w_i)$ $(1 \leq i \leq p)$.

A stochastic version of the Expectation-Maximization (EM) algorithm is used to estimate the vector parameter $\theta$ of the numerical model NM. Because of the nonlinearity of the model, the E step of the EM algorithm is intractable. A stochastic version of the EM algorithm, namely the Monte-Carlo Markov Chain Stochastic Approximation Expectation-Maximization (MCMC-SAEM) algorithm is used.

In order to ensure the theoretical convergence of the MCMC SAEM algorithm, the parameters of the model are considered as realizations of independents Gaussian random variables, which is equivalent to ensure that the model belongs to the curved exponential family.

This approach yields to the following hypothesis:

$p_0$ follows a probability distribution according to $\mathcal{N}(\overline{p_0}, \sigma_{p_0}^2)$, $\overline{p_0}$ and $\sigma_{p_0}^2$ being the mean and variance of the Gaussian distribution respectively, $t_0$ follows a probability distribution $\mathcal{N}(\overline{t_0}, \sigma_{t_0}^2)$, $\overline{t_0}$ and $\sigma_{t_0}^2$ being the mean and variance of the Gaussian distribution respectively, $v_0$ follows a probability distribution $\mathcal{N}(\overline{v_0}, \sigma_{v_0}^2)$, $\overline{v_0}$ and $\sigma_{v_0}^2$ being the mean and variance of the Gaussian distribution respectively, for all k, $\delta_k$ follows a probability distribution $\mathcal{N}(\overline{\delta_k}, \sigma_\delta^2)$, $\overline{\delta_k}$ and $\sigma_\delta^2$ being the mean and variance of the Gaussian distribution respectively, and matrix A is assumed to be writable as $A = \Sigma_{k=1}^{(N-1)N_s} c_k A_k$ where, for all k, $c_k$ following a probability distribution according to $\mathcal{N}(\overline{c_k}, \sigma_c^2)$, $\overline{c_k}$ and $\sigma_c^2$ being the mean and variance of the Gaussian distribution respectively, $A_k$ being an orthonormal basis of the sub-space in $T\{\gamma_\delta(t_0) \mathbb{M}\}$ that is orthogonal to $\dot{\gamma}(t_0)$ obtained using a Gram-Schmidt process. Under this hypothesis, the random variables $c_1, \ldots, c_{(N-1)N_s}$ are considered hidden variables for the model. The previous hypothesis relative to matrix A ensures the orthogonality condition on the columns of A. The orthogonality condition ensures that a point on the parallel curve $\eta^{w_i}(\gamma, .)$ moves at the same pace as in the average trajectory, so only the parameters of the time-reparameterization function accounts for the difference in the dynamics of the progression across the subjects. This property is crucial to ensure a unique decomposition between the spatial and temporal components, and thus the identifiability of the model.

Therefore, under the previous hypotheses, the vector parameter $\theta$ of the model is:

$$\theta = (\overline{p_0}, \overline{t_0}, \overline{v_0}, (\overline{\delta_k})_{1 \leq k \leq N-1}, (\overline{c_k})_{1 \leq k \leq (N-1)N_s}, \sigma_\eta, \sigma_\tau, \sigma)$$

whereas the hidden variables z of the model are:

$$z = (p_0, t_0, v_0, (\delta_k)_{1 \leq k \leq N-1}, (c_k)_{1 \leq k \leq (N-1)N_s}, (\eta_i)_{1 \leq i \leq p}, (s_{j,i})_{1 \leq j \leq N_s, 1 \leq i \leq p})$$

To obtain the vector parameter $\theta$ and hidden variables z, the MCMC-SAEM is iterated, until convergence, between three sub-steps: a first sub-step of simulation, a second sub-step of stochastic approximation and a third sub-step of maximization.

Let k be an integer greater than 1 and $\theta^{(k-1)}$ (respectively $z^{(k-1)}$) denote the parameters (respectively the hidden variables) at the (k−1)-th iteration of the algorithm.

The k-th iteration can be described as follows.

At the sub-step of simulation, $z^{(k)}$ is sampled from the transition kernel of an ergodic Markov Chain whose stationary distribution is the conditional distribution of the hidden variables knowing the observations $y = (y_{i,j})_{i,j}$ and the current estimates of the parameters $\theta^{(k-1)}$. This sampling is done by using a Hasting-Metropolis technique within a Gibbs sampler scheme.

At the sub-step of stochastic approximation, the stochastic approximation is done by calculating sufficent statistics as follows:

$$S^{(k+1)} \leftarrow S^{(k)} + \varepsilon_k(S(y, z^{(k)}) - S^{(k)})$$

where $(\varepsilon_k)_k$ is a decreasing sequence of positive step sizes.

In other words, the stochastic approximation sub-step consists in a stochastic approximation on the complete log-likelihood log $q(y, z|\theta)$ summarized as follows:

$$Q_t(\theta) = Q_{t-1}(\theta) + \varepsilon_t[\log q(y, z|\theta) - Q_{t-1}(\theta)],$$

where $(\varepsilon_t)_t$ is a decreasing sequence of positive step-sizes in $]0, 1]$ which satisfies $\Sigma_t \varepsilon_t = +\infty$ and $\Sigma_t \varepsilon_t^2 < +\infty$.

At the sub-step of maximization, parameters updates are obtained in closed form from the stochastic approximation on the sufficient statistics.

For instance, the parameter estimates are updated in the maximization step according to the following formula:

$$\Theta^{(t+1)} = \arg\max_{\theta \in \Theta}[Q_t(\theta)]$$

In summary, it has been disclosed a generic hierarchical spatiotemporal model for longitudinal manifold-valued data. The data consist in repeated measurements over time for a group of individuals. This numerical model NM enables estimating a group-average trajectory of progression, considered as a geodesic of a given Riemannian manifold. Individual trajectories of progression are obtained as random variations, which consist in parallel shifting and time reparametrization, of the average trajectory. These spatiotemporal transformations allow the applicant to characterize changes in the direction and in the pace at which trajectories are followed. The parameters of the model are estimated using a stochastic approximation of the expectation-maximization (EM) algorithm, the Monte Carlo Markov Chain Stochastic Approximation EM (MCMC SAEM) algorithm.

Experimental results obtained with the numerical model NM are illustrated in the experimental section.

Thus, at the end of the step of providing S32, both first data and a numerical model NM are obtained.

At the step of converting S34, the first data are converted into at least one point on the same Riemann manifold RM.

At the step of using S36, the numerical model NM is used to determine a temporal progression for the Alzheimer's disease for the studied subject.

These steps S34 and S36 are difficult to carry out so far as it requires to adapt (personalize) the parameters of the NM so that the trajectory of progression passes through, or as close as possible, to the first data converted as points on the Riemann manifold RM.

For instance, one may use the parameters of dispersion of the NM to generate series of trajectories on the Riemann manifold RM, which derives from the average trajectory by spatiotemporal transformations, such as the curves $C_1$ and $C_2$ in the example of FIG. 4. The point(s) to which the first data correspond in the Riemann manifold RM are used to select the curve which minimizes a distance with these points.

If the distance with the first curve $C_1$ is the smallest, it is determined that the expected temporal progression for the Alzheimer's disease for the studied subject is the first curve $C_1$.

The present invention therefore enables to determine the temporal progression of a biological phenomenon based on data taken from a subject.

The present method provides a good versatility in so far as the Riemannian manifold RM and its metric are chosen a priori, which allows us to introduce anatomical, physiological constraints into the model. The definition of the generic spatiotemporal model requires no other choice. The models which are introduced herein are based on the concept of parallel curves on a manifold. The random effects of the model allow to spatially and temporally register individual trajectories of progression.

In addition, it should be stressed that the proposed method for determining is particularly easy to implement in so far as no constraints are imposed on the first data.

Given the complexity of the problem to address, it could have been indeed expected that constraints be imposed on the data to provide. In particular, there is no need to data taken at specific time points. As a specific example, there is no need to obtain data at a specific reference time, such as the date at which disease starts.

Furthermore, the present method for determining a temporal progression is usable in multiple applications.

For instance, such method for determining a temporal progression is used in a method for predicting that a subject is at risk of suffering from a disease.

The method for predicting comprises carrying out the steps of the method for determining the temporal progression of a biological phenomenon which may affect a studied subject, the biological phenomenon being the disease, to obtain a first temporal progression. The method for predicting also comprises predicting that the subject is at risk of suffering from the disease based on the first temporal progression.

According to a specific embodiment, the method for predicting further provides when specific symptom are expected to occur for the subject.

According to another example, the method for determining a temporal progression is used in a method for diagnosing a disease.

The method for diagnosing comprises carrying out the steps of the method for determining the temporal progression of a biological phenomenon which may affect a studied subject, the biological phenomenon being the disease, to obtain a first temporal progression. The method for diagnosing also comprises a step for diagnosing the disease based on the first temporal progression.

According to another example, the method for determining a temporal progression is used in a method for identifying a therapeutic target for preventing and/or treating a pathology.

The method for identifying a therapeutic target comprises carrying out the steps of the method for determining the temporal progression of a biological phenomenon which may affect a studied subject, the first data being data relative to a subject suffering from the pathology, to obtain a first temporal progression.

The method for identifying a therapeutic target also comprises carrying out the steps of the method for determining a temporal progression which may affect a studied subject, the first data being data relative to a subject not suffering from the pathology, to obtain a second temporal progression.

The method for identifying a therapeutic target also comprises a step of selecting a therapeutic target based on the comparison of the first and second temporal progressions.

In such context, the term «therapeutic target» should be construed broadly as encompassing selecting specific kind of patients.

According to yet another example, the method for determining is used in a method for identifying a biomarker.

The biomarker may vary according to the specific example considered. For instance, the biomarker is a diagnostic biomarker of a pathology. In variant, the biomarker is susceptibility biomarker of a pathology, a prognostic biomarker of a pathology or a predictive biomarker in response to the treatment of a pathology.

The method for identifying a biomarker comprises carrying out the steps of the method for determining the temporal progression of a biological phenomenon which may affect a studied subject, the first data being data relative to a subject suffering from the pathology, to obtain a first temporal progression.

The method for identifying a biomarker also comprises carrying out the steps of the method for determining the temporal progression of a biological phenomenon which may affect a studied subject, the first data being data relative to a subject not suffering from the pathology, to obtain a second temporal progression.

The method for identifying a biomarker also comprises a step of selecting a biomarker based on the comparison of the first and second temporal progressions.

According to another example, the method for determining is used in a method for screening a compound useful as a medicine.

The compound has an effect on a known therapeutical target, for preventing and/or modifying and/or treating a pathology.

The method for screening comprises carrying out the steps of the method for determining the temporal progression of a biological phenomenon which may affect a studied subject, the first data being data relative to a to a subject suffering from the pathology and having received the compound, to obtain a first temporal progression.

The method for screening also comprises carrying out the steps of the method for determining the temporal progression of a biological phenomenon which may affect a studied subject, the first data being data relative to a subject suffering from the pathology and not having received the compound, to obtain a second temporal progression. The method for identifying a therapeutic target also comprises a step of selecting a therapeutic target based on the comparison of the first and second temporal progressions.

Each previously described application illustrate the possibility of the proposed method for determining a temporal progression.

The embodiments and alternative embodiments considered here-above can be combined to generate further embodiments of the invention.

Experimental Section

The numerical model NM is used to analyze the temporal progression of a family of biomarkers. This progression model estimates a normative scenario of the progressive impairments of several cognitive functions, considered here as biomarkers, during the course of Alzheimer's disease. The estimated average trajectory provides a normative scenario of disease progression. Random effects provide unique insights into the variations in the ordering and timing of the succession of cognitive impairments across different individuals.

Data Considered

The neuropsychological assessment tests "ADAS-Cog 13" from the ADNI1, ADNIGO or ADNI2 cohorts of the Alzheimer's Disease Neuroimaging Initiative (ADNI) was used. These tests are notably available at the internet address https://ida.loni.usc.edu/.

The "ADAS-Cog 13" consists of 13 questions, which allow testing the impairment of several cognitive functions. For the purpose of our analysis, these items are grouped into four categories: memory (5 items which are items 1, 4, 7, 8 and 9), language (5 items which are items 2, 5, 10, 11 and 12), praxis (2 items which are items 3 and 6) and concentration (1 item which is item 13).

248 individuals were included in the study. These 248 individuals were diagnosed with mild cognitive impairment at their first visit and the diagnosis changed to Alzheimer's disease before their last visit. There is an average of 6 visits per subjects, with an average duration of 6 or 12 months between consecutive visits. The minimum number of visits was 3 and the maximum number of visit was 11.

For the Experiments of FIGS. 8 to 12

According to a first case, the score of each item was normalized by the maximum possible score. Consequently, each data point of each individual consists in thirteen normalized scores, which can be seen as a point on the manifold $\mathbb{M}=]0, 1[^{13}$.

In the case where $\mathbb{M}=]0, 1[^{13}$, the number of independent sources $N_s$ can be any integer between 1 and 12. The choice of the number of independent sources influences the number of parameters to be estimated, which equals $9+12*N_s$. In order to keep a reasonable runtime, three experiments were conducted with $N_s$ equal to 1, 2 and 3. For each experiment, the MCMC-SAEM algorithm was run five times with different initial parameters. Only the experiment which returned the smallest residual noise variance was kept. Increasing the number of sources allowed to decrease the residual noise among the experiments: $\sigma^2=0.02$ for $N_s=1$, $\sigma^2=0.0162$ for $N_s=2$ and $\sigma^2=0.0159$ for $N_s=3$. Because the residual noise was almost similar for $N_s=2$ and $N_s=3$ sources, the results obtained with the less complex model are described. As a consequence, the results obtained with two independent sources are further developed below.

Figure 8:
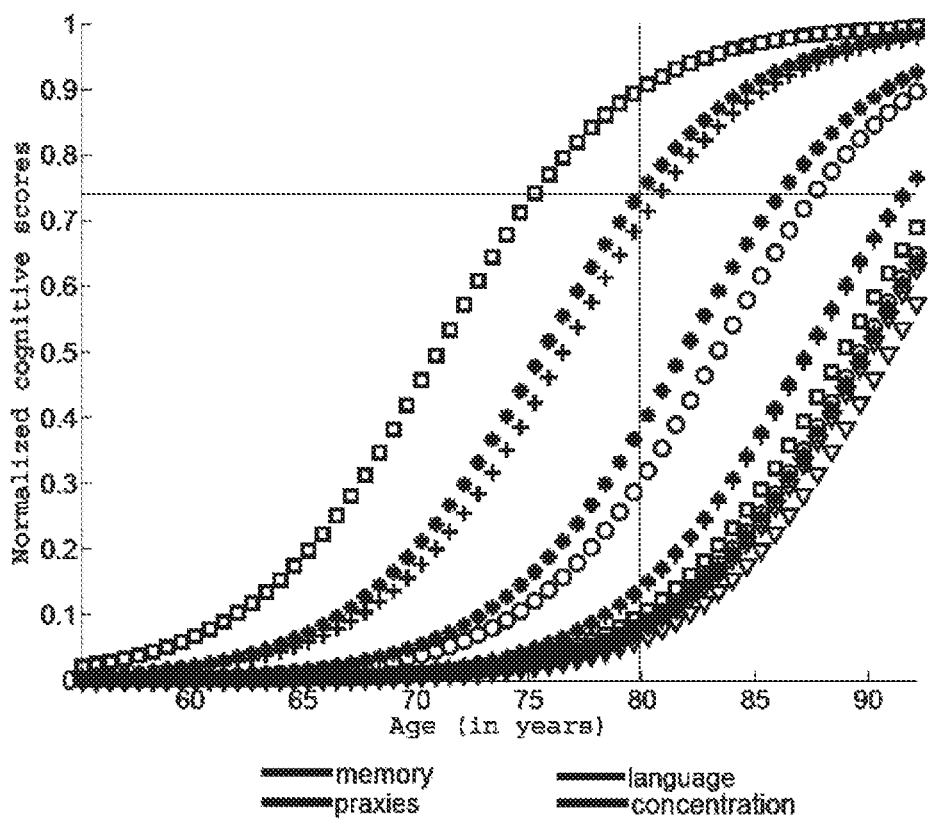
FIGS. 8 to 16 show schematically experimental results obtained by using the numerical model of FIGS. 5 to 7.

The average trajectory $\gamma_\delta$ is given in FIG. 8, where each curve represents the temporal progression of one specific item of the ADAS-Cog test. The estimated fixed effects are $p_0=0.74$, $t_0=79.88$ years, $v_0=0.047$ unit per year, and in years:

$$\delta=[0;-14;-11;4.6;-13;-14;-7.7;-0.9;-14.4;-14.05;-11.80;-15.3292]$$

This means that, on average, the memory-related items (items 1, 4, 7, 8, 9) reach the value $p_0=0.74$ at respectively $t_0$, $t_0-\delta_4$, $t_0-\delta_7$, $t0-\delta_8$ and $t0-\delta_9$ years, which correspond to respectively 79.88, 75.2, 87.6, 80.7 and 94.3 years. The concentration item reaches the same value at $t_0-\delta_{13}=86.1$ years. The progression of the concentration item is followed by praxis and language items.

Random effects show the variability of this average trajectory within the studied population. The standard deviation of the time-shift equals $\sigma_\tau=8.3$ years, meaning that the disease progression model in FIG. 8 is shifted in time by at most ±8.3 years for 95% of the population. This accounts for the variability in the age at disease onset among the population. The effects of the variance of the acceleration factors and the two independent components of the space-shifts are illustrated in FIG. 10.

Figure 10:
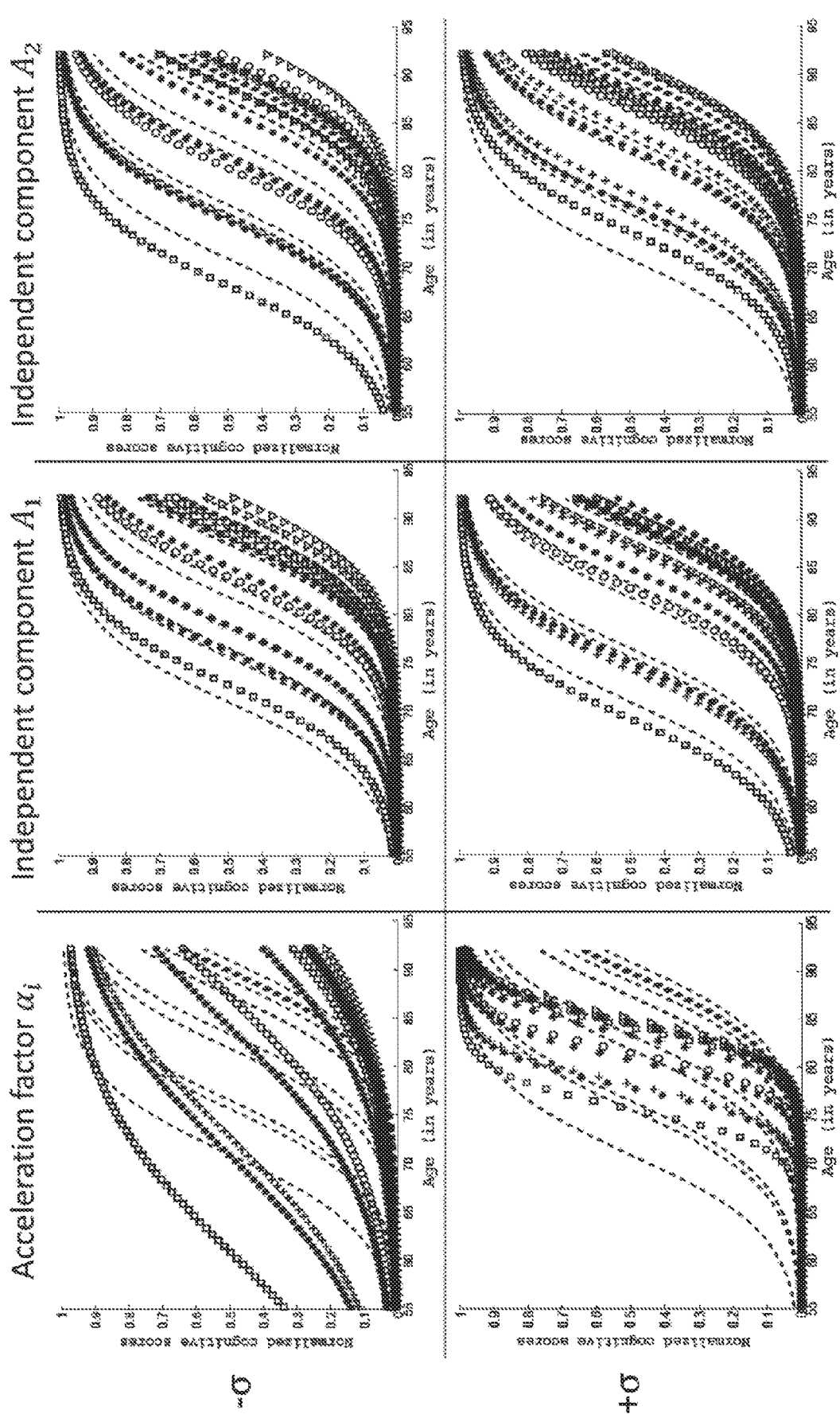

The first column of FIG. 10 illustrates the variability in pace of disease progression (the time-shifts are assumed to be zero in order to illustrate the effect of acceleration factor only). This variability is encoded by the variance $\sigma_\eta=0.8$ of the log-acceleration factor.

The first and second independent components illustrates the variability in the relative timing of the cognitive impairments.

The first independent direction shows that some memory items and language items are shifted in time with respect to the other ones, especially for memory item 4 ( ) and item 7 (°). The ordering of the memory item 7 (°) and the concentration item is inverted for individuals with a space shift $w_i=-\sigma_{s_{i,j}}A_1$. For those individuals, praxies items are impaired later, after the language items 2(*), items 12 (Δ) and item 5 ( ).

The second independent component shows a greater variability for the memory-related items than for the first independent components, in particular for memory item 9 (Δ) and item 4 ( ). For individuals with a space shift $w_i = -\sigma_{s_{i2}} A_2$, language-related items might be impaired later than the average individual, especially for the language item 12 (Δ).

Figure 9:
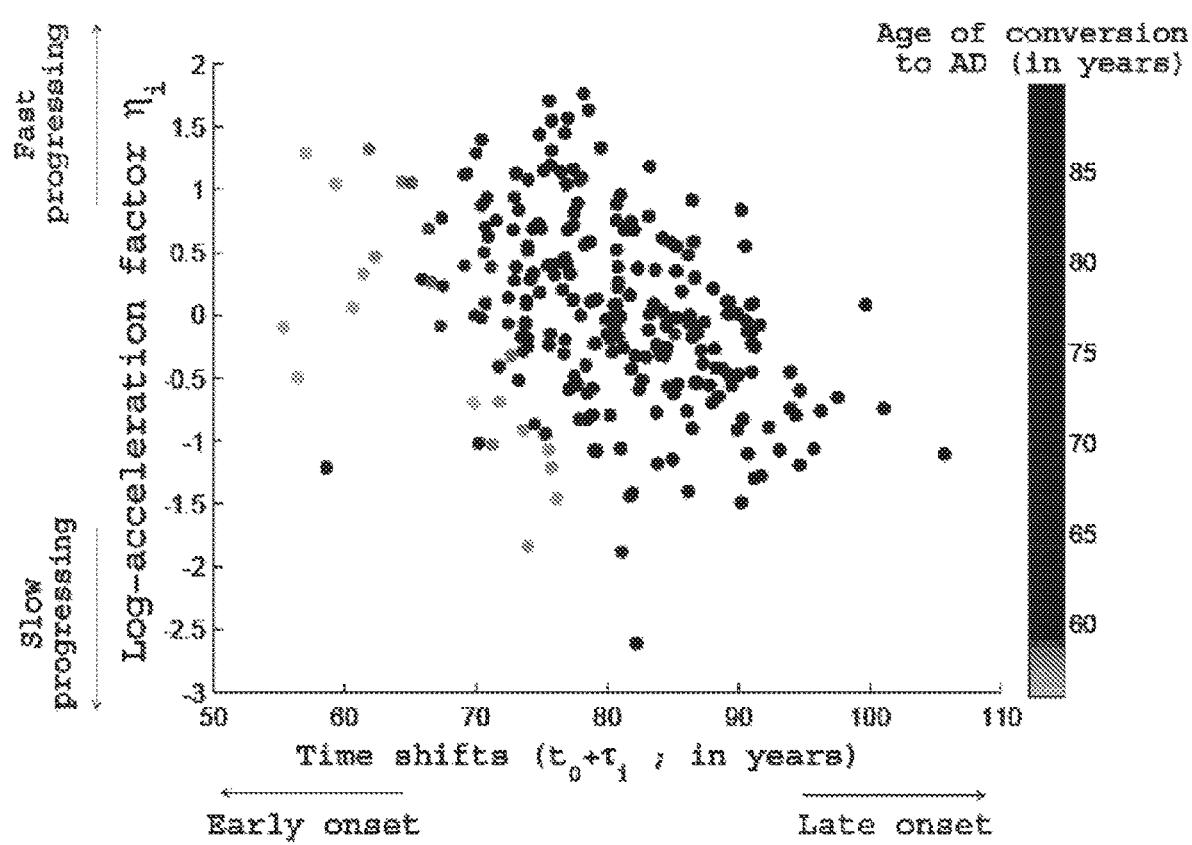

The subject-specific random effects estimated for each individual are obtained from the sampling step of the last iteration of the MCMC-SAEM and are plotted in FIG. 9. The FIG. 9 shows that the individuals who have a positive (respectively negative) time shift (they are evolving ahead, respectively behind, the average trajectory) are the individuals who converted late (respectively early) to Alzheimer's disease. This means that the individual time-shifts correspond well to the age at which a given individual was diagnosed with Alzheimer's disease. It is also to be noted that there is a negative correlation, equal to −0.4, between the estimated log-acceleration factors and time shifts. There is a tendency for early onset patients to be fast progressers.

Through its subject-specific affine reparametrization, the age of a given individual is registered to the common timeline of the average scenario.

Figure 11:
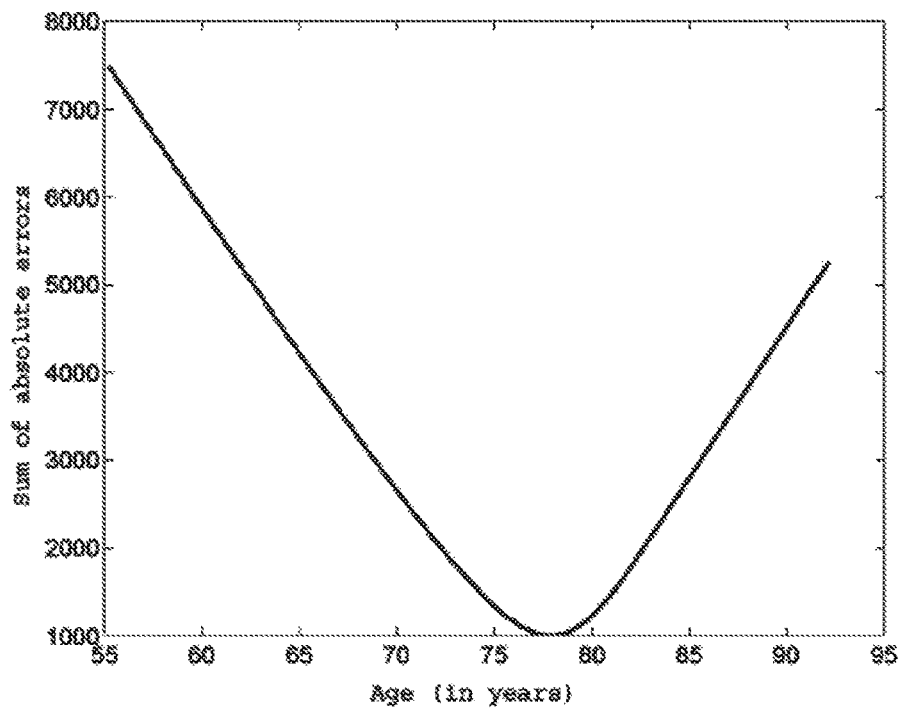

In FIG. 11, the evolution of the sum of the absolute errors with time is represented. In this case, the sum of the absolute errors is $\Sigma_i |t_i^{diag} - \psi_i^{-1}(t)|$ where $t_i^{diag}$ corresponds to the age at which the i-th individual converted to Alzheimer's disease. As apparent on FIG. 11, the sum of the absolute errors shows a unique minimum at t*=77.45 years. This age can be understood as the age of symptoms onset in the timeline of the normative scenario of disease progression.

Figure 12:
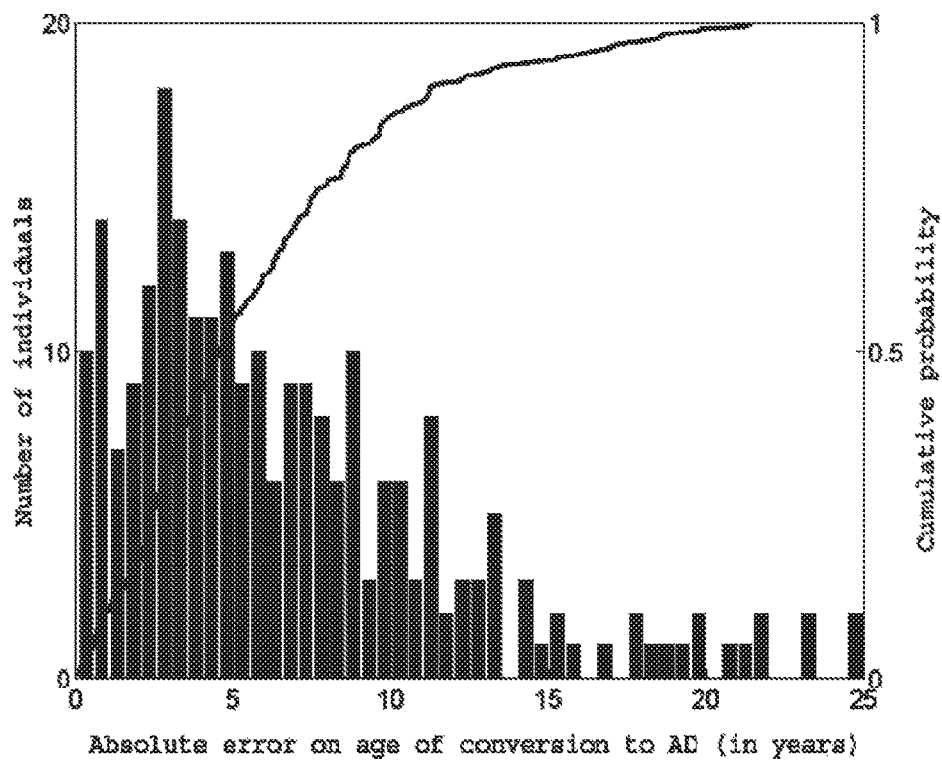

FIG. 12 corresponds to a histogram giving the number of individuals with relation to the absolute errors on the age of conversion to Alzheimer's disease in years. In other words, the histogram of FIG. 12 gives the number of individuals in function of the absolute error which is $|t_i^{diag} - \psi_i^{-1}(t^*)|$. The analysis of the histogram of FIG. 12 shows that the age $\psi_i^{-1}(t^*)$ is a prediction of the true age of conversion: the error of prediction is less than 5 years for 50% of the population. This prediction is all the more remarkable as this prediction is obtained by analyzing cognitive scores, which are inherently noisy and whose reproducibility is limited.

For the Experiments of FIGS. 13 to 16

According to a second case, scores within each category are added and normalized by the maximum possible score. Consequently, each data point consists in four normalized scores, which can be seen as a point on the manifold $\mathbb{M} = ]0, 1[^4$.

The model was applied with $N_s = 1$, 2 or 3 independent sources. In each experiment, the MCMC SAEM was run five times with different initial parameter values. The experiment which returned the smallest residual variance $\sigma^2$ was kept. The maximum number of iterations was arbitrarily set to 5000 and the number of burn-in iterations was set to 3000 iterations. The limit of 5000 iterations is enough to observe the convergence of the sequences of parameters estimates. As a result, two and three sources allowed to decrease the residual variance better than one source ($\sigma^2 = 0.012$ for one source, $\sigma^2 = 0.08$ for two sources and $\sigma^2 = 0.084$ for three sources). The algorithm was implemented in MATLAB® without any particular optimization scheme. The 5000 iterations required approximately one day.

The number of parameters to be estimated was equal to $9 + 3*N_s$. Therefore, the number of sources did not dramatically impact the runtime. Simulation was the most computationally expensive part of the algorithm. For each run of the Hasting-Metropolis algorithm, the proposal distribution was the prior distribution.

For a matter of clarity and because the results obtained with three sources were similar to the results with two sources, the experimental results obtained with two independent sources are further detailed.

Figure 13:
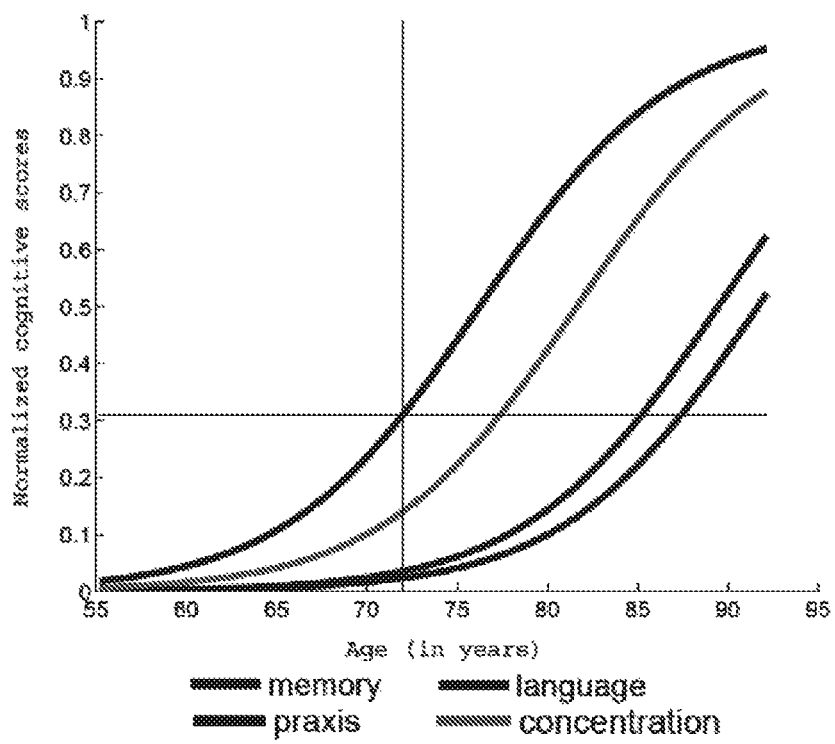

The average model of disease progression $y_\delta$ is plotted on FIG. 13. FIG. 13 is a graph showing the evolution with the age of the memory, language, praxis and concentration in terms of normalized cognitive score. The four curves represented correspond to the estimated average trajectory. A vertical line is drawn at $t_0 = 72$ years old and a horizontal line is drawn at $p_0 = 0.3$.

When analyzing FIG. 13, it appears that the estimated fixed effects are $p_0 = 0.3$, $t_0 = 72$ years, $v_0 = 0.04$ unit per year, and $\delta = [0; -15; -13; -5]$ years. This means that, on average, the memory score (first coordinate) reaches the value $p_0$ at $t_0 = 72$ years, followed by concentration which reaches the same value at $t_0 + 5 = 77$ years, and then followed by praxis and language at the age of 85 and of 87 years respectively.

Random effects show the variability of this average trajectory within the studied population. The standard deviation of the time-shift equals $\sigma_T = 7.5$ years, meaning that the disease progression model in FIG. 13 is shifted by ±7.5 years to account for the variability in the age of disease onset. The effects of the variance of the acceleration factor $\alpha_i$, and the two independent components $A_1$ and $A_2$ of the space-shifts are illustrated in FIG. 15.

Figure 15:
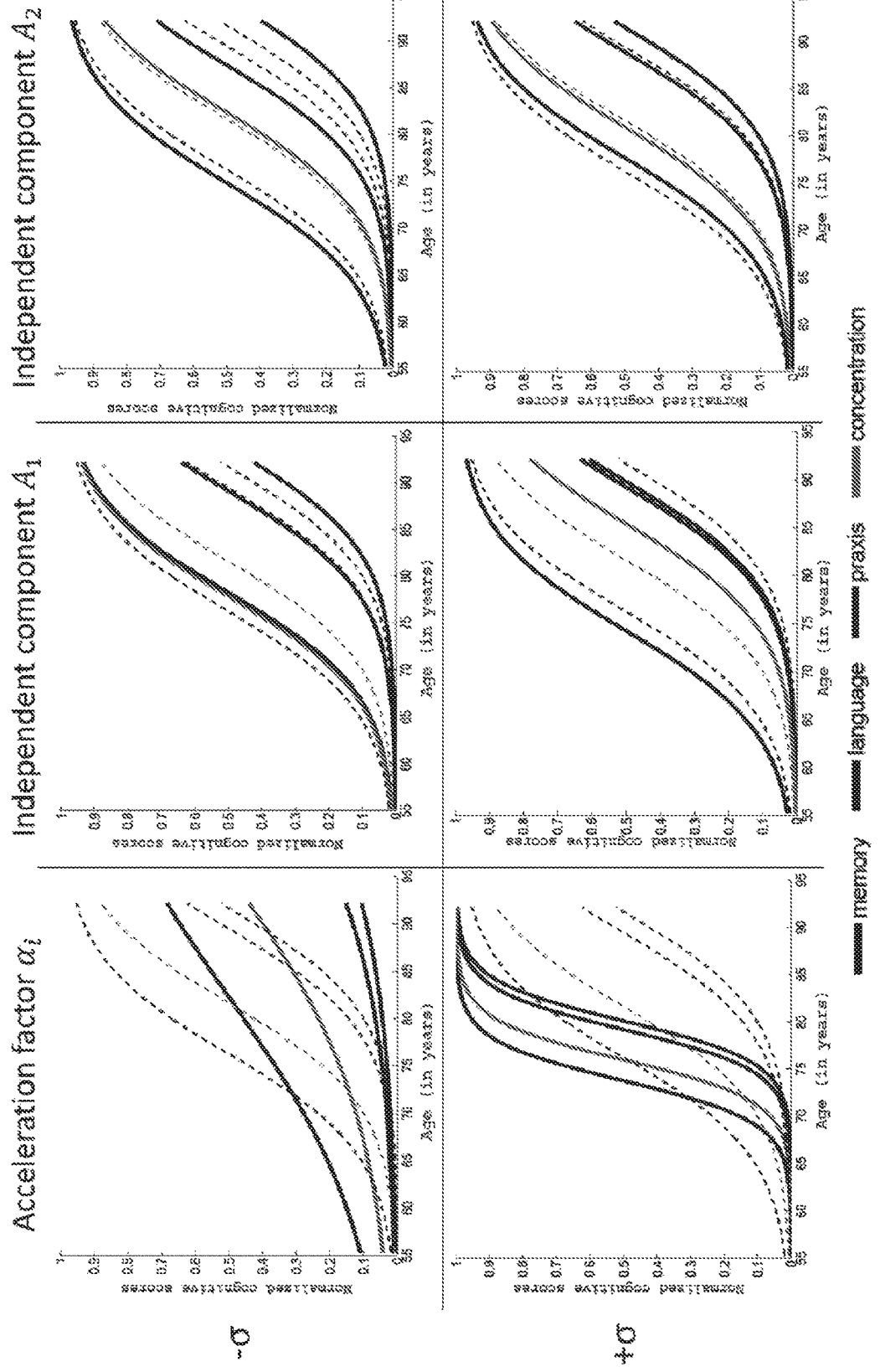

FIG. 15 is a series of six graphs illustrating the variability in disease progression superimposed with the average trajectory $y_\delta$ (dotted lines).

On the first column, the effects of the acceleration factor $\alpha_i$ with plots of $y_\delta(\exp(\pm\sigma_\eta)(t-t_0)+t_0)$ are represented. The acceleration factor $\alpha_i$ shows the variability in the pace of disease progression, which ranges between 7 times faster and 7 times slower than the average.

On the second column, the effects of the first independent component of space-shift with plots of $$\eta^{\pm\sigma_{s_1},A_1}(\gamma_\delta,.)$$

are illustrated. The first independent component $A_1$ shows variability in the relative timing of the cognitive impairments: in one direction, memory and concentration are impaired nearly at the same time, followed by language and praxis; in the other direction, memory is followed by concentration and then language and praxis are nearly superimposed.

On the third column, the effects of the first independent component of space-shift with plots of $$\eta^{\pm\sigma_{s_2},A_2}(\gamma_\delta,.)$$

are represented. The second independent component $A_2$ keeps almost fixed the timing of memory and concentration, and shows a great variability in the relative timing of praxis and language impairment. It shows that the ordering of the last two may be inverted in different individuals. Overall, these space-shift components show that the onset of cognitive impairment tends to occur by pairs: memory and concentration followed by language and praxis.

Figure 14:
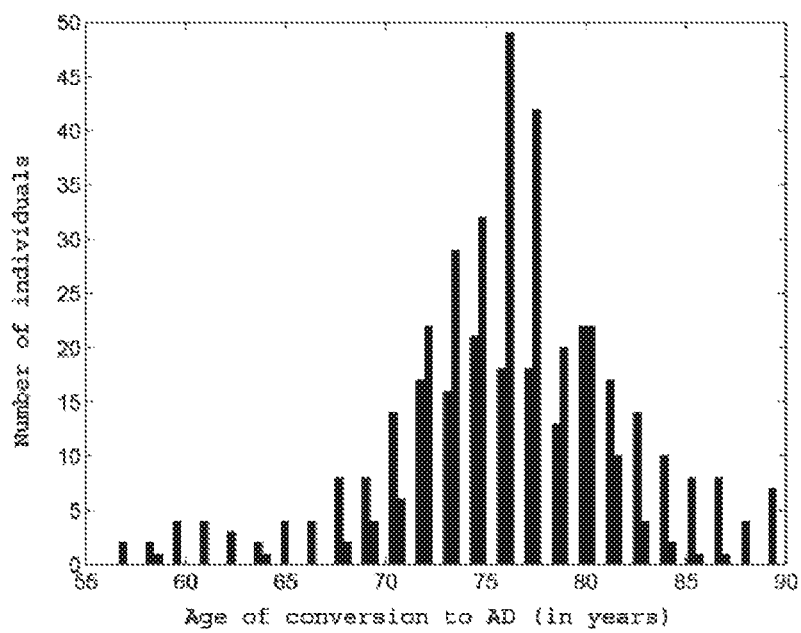
Figure 16:
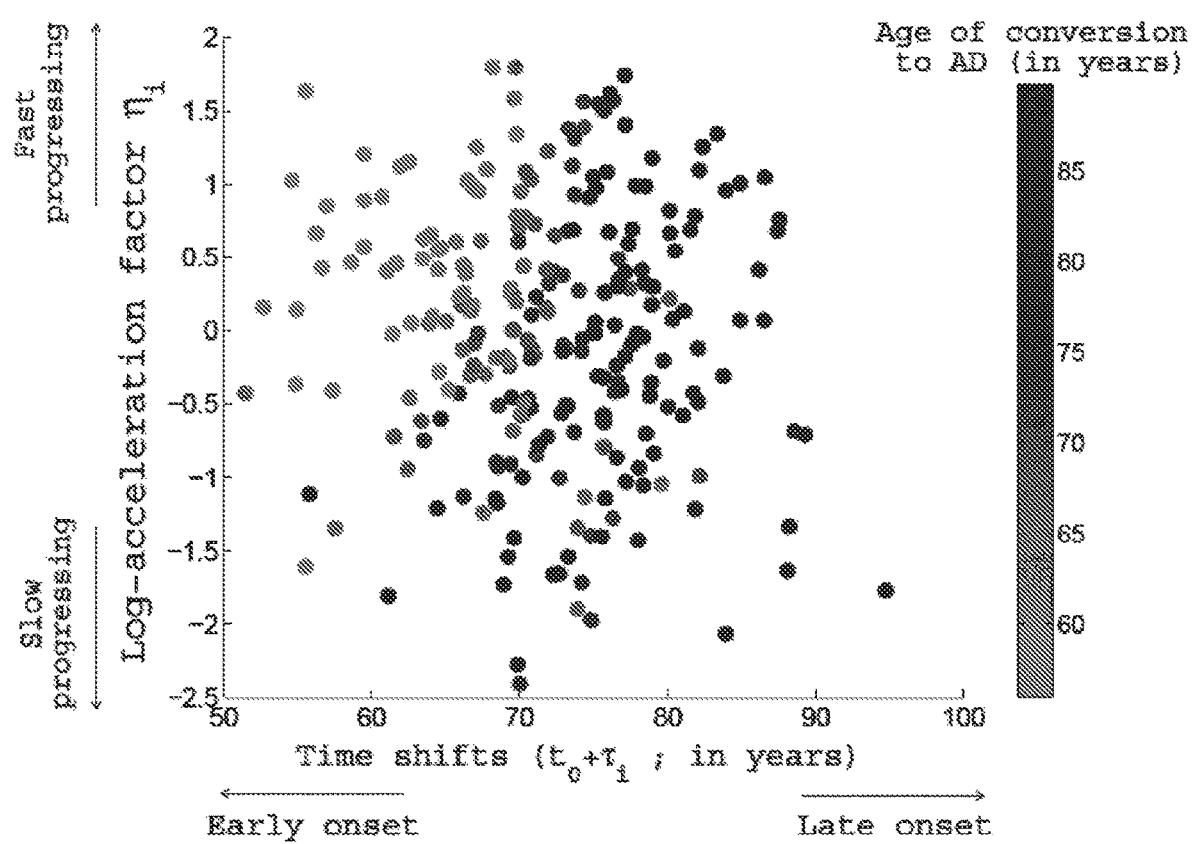

Estimates of the random effects for each individual are obtained from the simulation step of the last iteration of the algorithm and are plotted in FIG. 16. In a similar way to FIG. 9, FIG. 16 shows that the estimated individual time-shifts correspond well to the age at which individuals were diagnosed with Alzheimer's disease. This means that the value $p_0$ estimated by the model is a good threshold to determine diagnosis (a fact that has occurred by chance), and more importantly that the time-warp correctly registers the dynamics of the individual trajectories so that the normalized age correspond to the same stage of disease progression across individuals. This fact is corroborated by FIG. 14 which shows that the normalized age of conversion to Alzheimer's disease is picked at 77 years old with a small variance compared to the real distribution of age of conversion. FIG. 14 is a histogram diagram of the ages of conversion to Alzheimer's disease with time-warp (grey bars) and the normalized ages of conversion to Alzheimer's disease (black bars).

The invention claimed is:

1. A method for determining the temporal progression of a biological phenomenon which may affect a studied subject, the method comprising:
providing first data, the first data being data relative to biomarkers for the studied subject, the biomarkers being relative to the progression of the biological phenomenon,
providing a numerical model (NM), the numerical model (NM) being a function in a Riemann manifold (RM), the numerical model (NM) associating to values of biomarkers a temporal progression trajectory for the biological phenomenon and data relative to the dispersion of the progression trajectory for the biological phenomenon among a plurality of subjects, the numerical model (NM) being obtained by using a stochastic approximation in an expectation-maximization technique on data relative to biomarkers taken at different time points for a plurality of subjects,
converting the first data into at least one point on the same Riemann manifold (RM), and
using the numerical model (NM) to determine a temporal progression for the biological phenomenon for the studied subject.

2. The method according to claim 1, wherein the biological phenomenon is a biological phenomenon whose temporal progression extends over more than three years.

3. The method according to claim 1, wherein the biological phenomenon is a neurodegenerative disease.

4. The method according to claim 1, wherein, when providing first data, the first data are data relative to neuropsychological biomarkers.

5. The method according to claim 1, wherein the studied subject is an animal.

6. The method according to claim 1, wherein when providing the numerical model (NM), the stochastic approximation in an expectation-maximization technique is a Monte-Carlo Markov Chain Stochastic Approximation Expectation-Maximization technique.

7. The method according to claim 1, wherein when providing the numerical model (NM), the number of subjects is superior or equal to 100.

8. The method according to claim 1, wherein, in the numerical model (NM), the data relative to the dispersion of the progression trajectory for the biological phenomenon among a plurality of subjects are provided as standard deviations of time for a plurality of values of biomarkers.

9. A method for predicting that a subject is at risk of suffering from a disease, the method for predicting comprising:
carrying out the method for determining the temporal progression of a biological phenomenon which may affect a studied subject to claim 1, the biological phenomenon being the disease, to obtain a first temporal progression, and
predicting that the subject is at risk of suffering from the disease based on the first temporal progression.

10. A method for treating a disease, the method for treating comprising:
carrying out the method for determining the temporal progression of a biological phenomenon which may affect a studied subject to claim 1, the biological phenomenon being the disease, to obtain a first temporal progression, and
administrating medicine to the studied subject targeting the disease obtained based on the first temporal progression.

11. A method for identifying a therapeutic target for preventing and/or treating a pathology, the method comprising:
carrying out the method for determining the temporal progression of a biological phenomenon which may affect a studied subject according to claim 1, the first data being data relative to a subject suffering from the pathology, to obtain a first temporal progression,
carrying out the method for determining the temporal progression of a biological phenomenon which may affect a studied subject according to claim 1, the first data being data relative to a subject not suffering from the pathology, to obtain a second temporal progression,
selecting a therapeutic target based on the comparison of the first and second temporal progressions.

12. A method for identifying a biomarker, the biomarker being a diagnostic biomarker of a pathology, a susceptibility biomarker of a pathology, a prognostic biomarker of a pathology or a predictive biomarker in response to the treatment of a pathology, the method comprising:
carrying out the method for determining the temporal progression of a biological phenomenon which may affect a studied subject according to claim 1, the first data being data relative to a subject suffering from the pathology, to obtain a first temporal progression,
carrying out the method for determining the temporal progression of a biological phenomenon which may affect a studied subject according to claim 1, the first data being data relative to a subject not suffering from the pathology, to obtain a second temporal progression,
selecting a biomarker based on the comparison of the first and second temporal progressions.

13. A method for screening a compound useful as a medicine, the compound having an effect on a known therapeutical target, for preventing and/or treating a pathology, the method comprising:
carrying out the method for determining the temporal progression of a biological phenomenon which may affect a studied subject according to claim 1, the first data being data relative to a subject suffering from the pathology and having received the compound, to obtain a first temporal progression,
carrying out the method for determining the temporal progression of a biological phenomenon which may affect a studied subject according to claim 1, the first data being data relative to a subject suffering from the pathology and not having received the compound, to obtain a second temporal progression, selecting a compound based on the comparison of the first and second temporal progressions.

14. A non-transitory computer-readable media having computer-executable instructions embodied thereon, wherein when executed by a computer device including a processor in communication with a memory, the computer-executable instructions cause the processor to carry out the steps of a method according to claim 1.

* * * * *